(12) United States Patent
Ritsche (10) Patent No.: US 6,446,839 B1
(45) Date of Patent: Sep. 10, 2002

(54) DISPENSER WITH MANUALLY OPERABLE DISCHARGE DEVICE

(75) Inventor: Stefan Ritsche, Radolfzell (DE)

(73) Assignee: Ing. Erich Pfeiffer GmbH, Radolfzell (DE)

( * ) Notice: Subject to any disclaimer, the term of this patent is extended or adjusted under 35 U.S.C. 154(b) by 0 days.

(21) Appl. No.: 09/641,049

(22) Filed: Aug. 17, 2000

(30) Foreign Application Priority Data

Aug. 25, 1999 (DE) .......................................... 199 40 236

(51) Int. Cl.[7] ................................................. B05B 11/00
(52) U.S. Cl. ..................................... 222/82; 222/153.13
(58) Field of Search ................................ 222/160, 162, 222/163, 81–83.5, 88, 153.06, 153.13

(56) References Cited

U.S. PATENT DOCUMENTS

| 4,921,142 A | * | 5/1990 | Graf et al. ................... 222/162 |
| 5,289,946 A | | 3/1994 | Fuchs |
| 5,427,280 A | | 6/1995 | Fuchs |
| 5,433,343 A | * | 7/1995 | Meshberg .................... 222/162 |
| 5,813,570 A | * | 9/1998 | Fuchs et al. ................... 222/82 |
| 6,045,008 A | * | 4/2000 | Gonzalez Fernandez et al. 222/153.13 |
| 6,059,150 A | | 5/2000 | Fuchs et al. |
| 6,257,457 B1 | | 7/2001 | Oechsel |

FOREIGN PATENT DOCUMENTS

| DE | 19753147 A1 | 6/1999 |
| EP | 0311863 B1 | 4/1989 |
| EP | 0 686 432 A2 | 12/1995 |
| EP | 00 11 6578 | 2/2002 |
| FR | 2 682 305 A1 | 4/1993 |
| JP | 6 171 698 | 6/1994 |
| WO | WO 91/13689 | 9/1991 |
| WO | WO 93/03857 | 3/1993 |
| WO | WO 98/30335 | 7/1998 |

* cited by examiner

*Primary Examiner*—J. Casimer Jacyna
(74) *Attorney, Agent, or Firm*—Quarles & Brady LLP (57) ABSTRACT

The invention relates to a dispenser for the discharge and the atomizing of media, in which a liquid medium is discharged in one charge or a small number of partial charges in one operating stroke of an operating presser or trigger. The dispenser is secured against accidental operation and has a minimum packing or storage volume. Prior to each stroke, the operating presser is returned from an operating end portion to the operating starting position to commence the discharge stroke.

23 Claims, 7 Drawing Sheets

DISPENSER WITH MANUALLY OPERABLE DISCHARGE DEVICE

FIELD OF APPLICATION AND PRIOR ART

DE 197 53 147 A1 discloses a dispenser for the discharge, particularly the atomizing of media, particularly liquid medicaments, which delivers a medicament charge in one or optionally a few strokes. Operation takes place between the fingers of the user, the thumb pressing an operating trigger or presser in the operating and discharge direction.

EP-B-311 863 describes a discharge device in which a pump cylinder and a resilient stop constructed in the manner of a snap locking means cooperate in such a way that prior to the performance of a partial stroke a specific operating pressure must be applied by the operator, so that after overcoming this pressure point the liquid is discharged with a specific minimum force and speed. This construction ensures that e.g. on atomizing the medium, from the outset an adequate atomizing pressure is present and that the pump is operated up to the end of its stroke and consequently delivers in one or two strokes the total content of the medium reservoir, which simultaneously forms the pump cylinder. Such single or multiple dosing means are important for the delivery of medicaments, which are particularly critical with respect to dosage, contamination, preserving or other criteria.

PROBLEM AND SOLUTION

The problem of the invention is to construct such dispensers in such a way that they are on the one hand secured against accidental operation and on the other have a minimum package or storage volume.

This problem is solved in that prior to each stroke the operating presser must be brought from an operating end position into the operating starting position.

Due to the fact that the operating presser is initially in its operating end position, an accidental operation of said operating presser is impossible. Simultaneously the packing space of the dispenser is reduced by the length of an operating stroke of the operating presser.

Particular preference is given to dispensers, which have a casing with a gripping surface shaped thereon for supporting at least one finger and with a discharge opening, the operating presser being guided in relatively movable manner with respect to the gripping surface in the casing.

Advantageously the relative movement between the operating presser and the casing is a linear movement.

It is also advantageous if the operating end position is fixed by a first stop limiting the stroke movement of the operating presser.

It is also advantageous if the operating starting position of the stroke movement is fixed by a second stop limiting the movement direction opposite to the stroke movement.

It is particularly advantageous to provide such dispensers with a discharge device comprising a thrust piston pump, whose pump cylinder is the reservoir for the medium to be discharged and according to an advantageous further development the pump cylinder comprises a cylindrical glass ampoule, which is placed in a sleeve.

The advantageous further developments of the invention relate to the catch acting between the pump cylinder and the casing and the drag mechanism acting between the operating presser and the pump cylinder, so as to prevent an undesired movement of the pump cylinder in a direction opposite to the stroke movement or during a pump stroke.

The movement of the operating presser from the operating end position into the operating starting position takes place, in a first embodiment, by manual action. The movement of the operating presser from the operating end position into the operating starting position takes place, in a second embodiment, as a result of a force reservoir or accumulator, which is preferably kept pretensioned in the operating end position, the pretensioned holding position being releasable by the operation of a release member and in this way the operating presser is moved from the operating end position into the operating starting position.

These and further features can be gathered from the claims, description and drawings and the individual features, either singly or in the form of sub-combinations, can be implemented in an embodiment of the invention and in other fields and can represent advantageous, independently protectable constructions for which protection is hereby claimed. The subdivision of the application into individual sections and the subtitles in no way restrict the general validity of the statements made thereunder.

BRIEF DESCRIPTION OF THE DRAWINGS

An embodiment of the invention is shown in the drawings and described hereinafter. This takes place by means of an example in which the total charge is discharged in two strokes. FIGS. 1 and 2 show a dispenser prior to the first operation, whilst FIGS. 3a, 3b to 7a and 7b in each case constitutes a sectional representation and a part sectional, perspective representation of a sequence of positions, as occur with a two-stroke operation of the dispenser.

Figure 1:
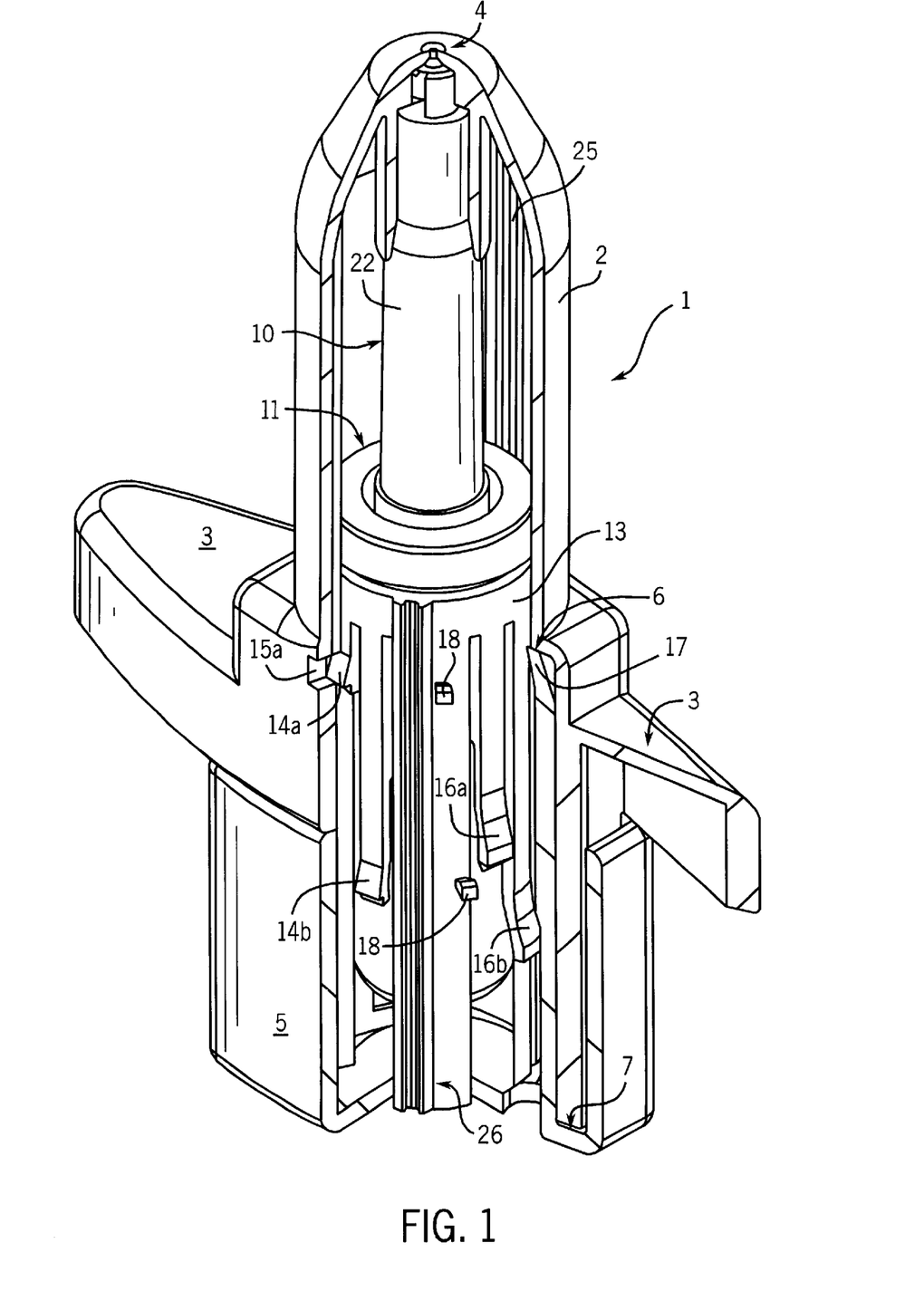
FIG. 1 is a part sectional, perspective view of a dispenser according to the invention prior to its initial operation.
Figure 2:
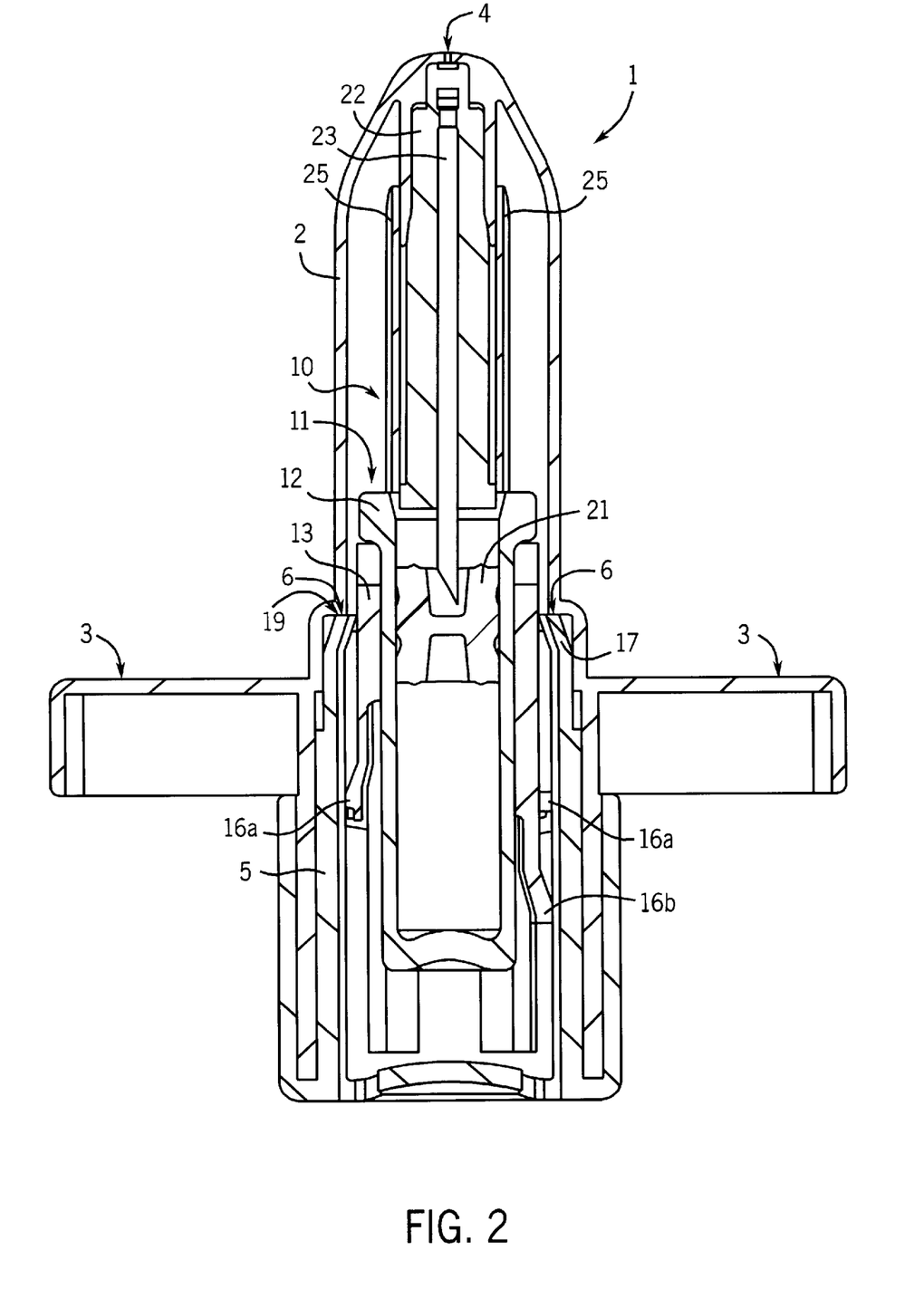
FIG. 2 is a sectional representation through a dispenser according to FIG. 1.

DESCRIPTION OF THE EMBODIMENT ACCORDING TO FIGS. 1 AND 2

FIG. 1 shows in a perspective, part sectional view a dispenser according to the invention, in which the operating trigger or presser 5 is in the operating end position prior to the first stroke. The dispenser 1 has a casing 2 on which are shaped gripping surfaces 3 for supporting at least one finger. A thrust piston pump 10 is placed in the casing 2 as the discharge device. The pump cylinder 11 of the thrust piston pump 10 is formed from a glass ampoule 12 held in a sleeve 13. The piston of the thrust piston pump is subject to the action of the shaft 22. The sleeve 13 has guide rails 26, which slide in casing-side guide grooves 25 and prevent a twisting of the sleeve 13 or a tilting between the shaft 22 and the pump cylinder 11. For operating the thrust piston pump 10 is provided the operating presser 5, which is located on the casing 2 in the axial direction of the thrust piston pump between two end positions defined by a first stop 6 and a second stop 7. The operating presser 5 in the same way as the casing 2 in the area below the gripping surface 3 has an approximately rectangular cross-section, which brings about a twist-proof and limited tilting guidance of the operating presser 5 on the casing 2. This design of the operating presser 5 also permits a good manual operability. It also provides the user in tactile form with information regarding the dispenser position.

In conjunction with the sleeve-side locking cam 14a, the casing-side locking hole 15a forms a locking means preventing a movement of the pump cylinder 11 in opposition to its stroke movement. To enable the locking connection between the casing 2 and the sleeve 13 to be released during a pump cylinder stroke, the locking cam is shaped on a spring web, the spring web and locking cam forming part of the sleeve 13.

During the stroke movement of the operating presser 5 there is a drag connection between the driver 17 of the operating presser and the spring web 16a, 16b constructed on the sleeve 13. The drag connection between the driver 17 and spring web 16b exists during the second stroke and only for as long as there is a stroke movement of the operating presser 5 operating the discharge device. Onto the sleeve 13 are shaped pressure point means 18 and between the latter and the sleeve 13 there is a predetermined breaking point. The function of the pressure point means 18 is to ensure that the discharge strokes in each case take place with a predetermined minimum pressure, the minimum pressure firstly ensuring that a stroke is performed in such a way that the operating presser 5 is transferred completely from the operating starting position II into the operating end position I and secondly ensures that the desired spray mist passes out of the discharge opening, where there are limited substance losses through drop formation in the vicinity of the discharge opening.

FIG. 2 shows the dispenser of FIG. 1 in a cross-section. The dispenser 1 with the casing 2 and the gripping surfaces shaped on the casing 2 and the discharge opening 4 formed in the casing 2 serve to receive the thrust piston pump 10. The thrust piston pump 10 comprises the pump cylinder 11, comprising the sleeve 13 and the glass ampoule 12 held therein, as well as the shaft 22 operating the piston 21. A needle 23 is placed in the shaft 22. The piston 21 also serves as a plug for the ampoule 12 and can be perforated by the needle 23.

On the casing 2 is formed a shearing edge 19 constituted by a step in the casing and which serves to shear the pressure point means 18 from the sleeve 13 if a stroke actuation of the operating presser 5 takes place with more than the necessary minimum force.

With respect to the longitudinal axis of the thrust piston pump 10, the operating presser 5 is axially displaceably mounted in the casing 2 and the shearing edge shaped on the casing 2 simultaneously forms a first stop 6 defining the operating end position between the operating presser 5 and casing 2. The second stop 7 securing the operating starting position results from a limitation of the displacement path of the operating presser in the casing. The sleeve 13 is positioned radially between the glass ampoule 12 and the inside of the operating presser 5. The overpressable spring webs 16a, 16b slide along the inside of the operating presser 5. For producing the drag connection between the pump cylinder 11 with the sleeve 13 and operating presser 5 is provided the driver 17 shaped on the operating presser 5.

DESCRIPTION OF THE FUNCTION BY MEANS OF FIGS. 3a, 3b TO 7a, 7b

Figures 3A, 3B:
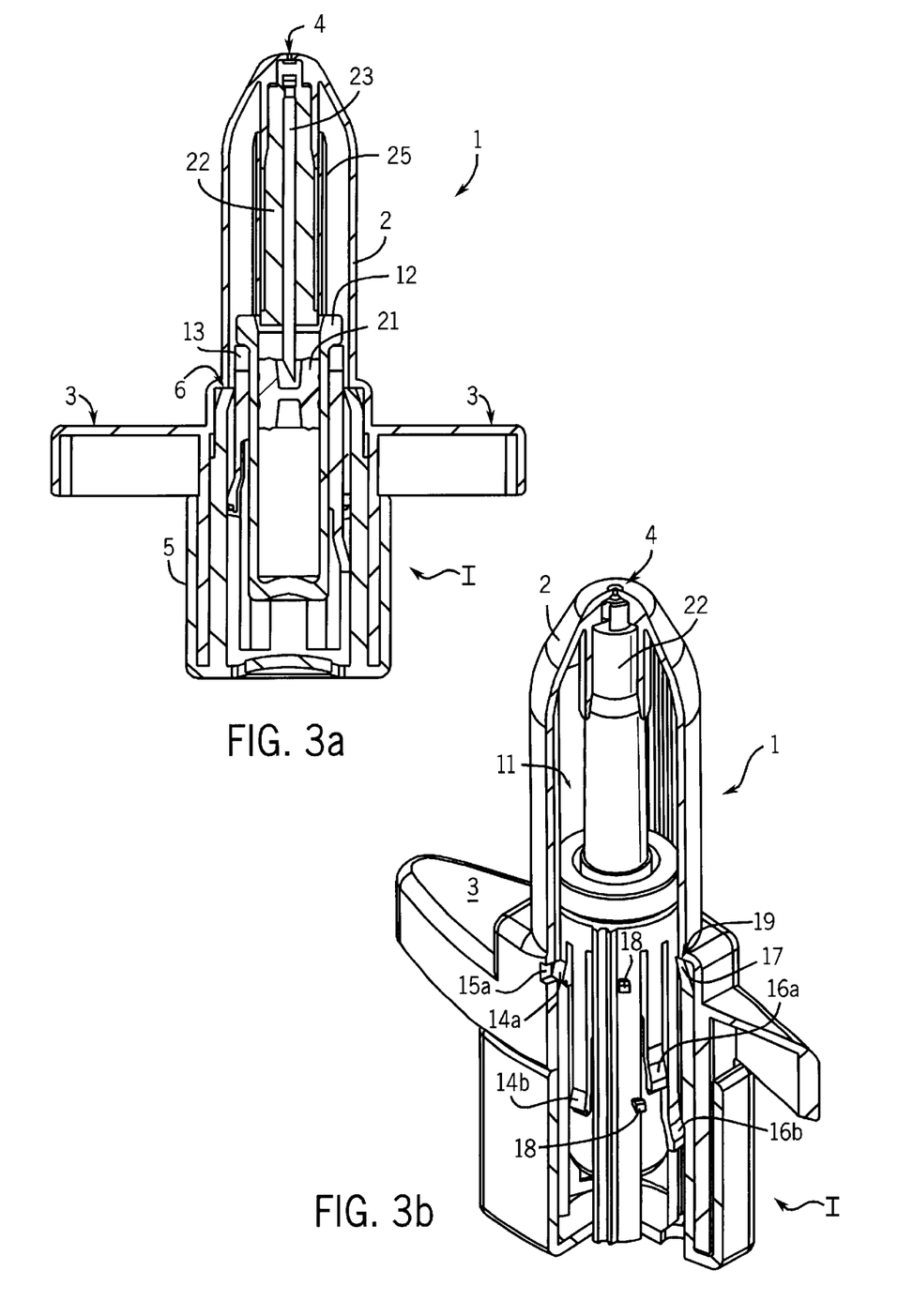
FIGS. 3a and 3b show the position prior to the first operation.

FIG. 3a shows the cross-section through a dispenser according to the invention, whilst FIG. 3b is a part sectional perspective view of the dispenser. In both cases the operating trigger or presser 5 is in the operating end position I, but as yet no stroke has taken place in which part of the charge or the entire charge would be discharged. In the represented position the dispenser 1 is protected against accidental operation. It also has a limited space requirement and can consequently be packed and stored with a limited packing volume.

Figures 4A, 4B:
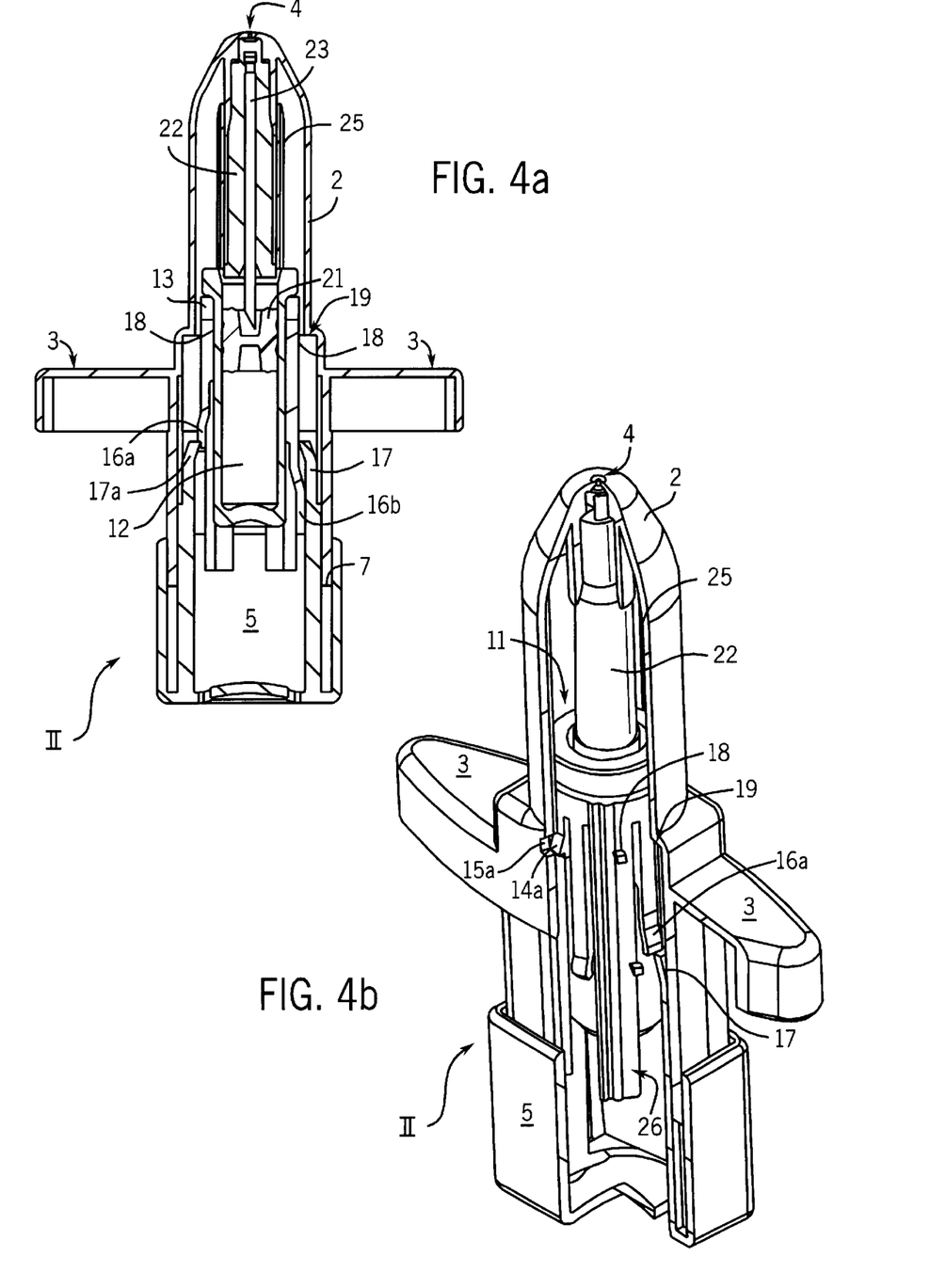
FIGS. 4a and 4b show the position of the operating presser in the operating starting position before the first stroke.

The operating end position I of the operating presser 5 is defined by the first stop 6 between the casing 2 and operating presser 5. No connection by drag means is provided between the operating presser 5 and sleeve 13 of the pump cylinder 11. The locking cam 14b and the spring webs 16a, 16b engaging on the inside on the operating presser 5 prevent with a limited clamping force the operating presser sliding from the operating end position, as shown, into the operating starting position II, as shown in FIGS. 4a and 4b, without there being a manual operation of the operating presser by the user. The locking cam 14a of sleeve 13 is locked in the locking hole 15a of casing 2 and it is consequently ensured that during a movement of the operating presser 5 from the operating end position I into the operating starting position II, i.e. a movement counter to a stroke of the thrust piston pump 10, no movement of the pump cylinder 11 occurs in the same direction. As is apparent from the sectional representation of FIG. 3a, the glass ampoule 12, held in the sleeve 13, is hermetically sealed by a plug, which simultaneously serves as a piston 21 of the thrust piston pump 10. The piston 21 has a perforation point for the needle 23, which is located in the shaft 22. The needle 23 serves as a discharge channel from the glass ampoule 12 to the discharge opening 4 in the casing 2, as soon as the piston 21 is perforated.

On the casing 2 are shaped gripping surfaces 3, which serve to support in each case one finger, e.g. the middle and index finger during the operation of the operating presser with the thumb in order to produce a stroke. As can be gathered from FIG. 3b, the shearing edge 19 on the casing 2 not only serves for the casing-side definition of the first stop 6 but also to shear off the pressure point means 18 by means of the shearing edge 19.

Through the manual operation of the operating presser 5 in opposition to the direction of a stroke, as used for the discharge of a partial charge, in the present case half the total charge, the operating starting position II shown in FIGS. 4a and 4b is reached. A discharge stroke has not yet taken place, but can now take place at any time. The position of the sleeve 13 with respect to the casing 2 is still secured by the locking cam 14a of sleeve 13 engaging in the locking hole 15a, so that a movement of the pump cylinder 11 counter to the stroke direction is still impossible. In the sliding guide of the operating presser 5 in casing 2 is formed a second stop 7 ensuring that the represented operating starting position II is not exceeded counter to the stroke direction over and beyond a certain tolerance and in this way separating the operating presser 5 from the casing 2. In the operating starting position II the sleeve-side drag means 16a formed by a spring web with a cam overpressable during the return stroke, and the operating presser-side drag means 17a engage on one another in such a way that during a stroke movement of the operating presser 5 the pump cylinder 11 is moved in the direction of the discharge opening 4. The locking between the locking cam 14a and the locking hole 15a is released during such a movement. Guided by the sleeve-side guide rail 26 and the casing-side guide groove 25, the sleeve 13 slides in twist-proof manner in the casing 2 in the direction of the discharge opening 4. The drag means for the second stroke formed by the spring web 16b and the driver 17*b* are not in engagement with one another. The sleeve-side pressure point means 18 engage on the shearing edge 19 of the casing 2 and must be sheared first during an operation of the thrust piston pump. The pressure point means 18 ensure that an operation of the operating presser only leads to a stroke if the operation takes place in such a way that there is a complete stroke movement transferring the operating presser 5 into the operating end position I.

Figures 5A, 5B:
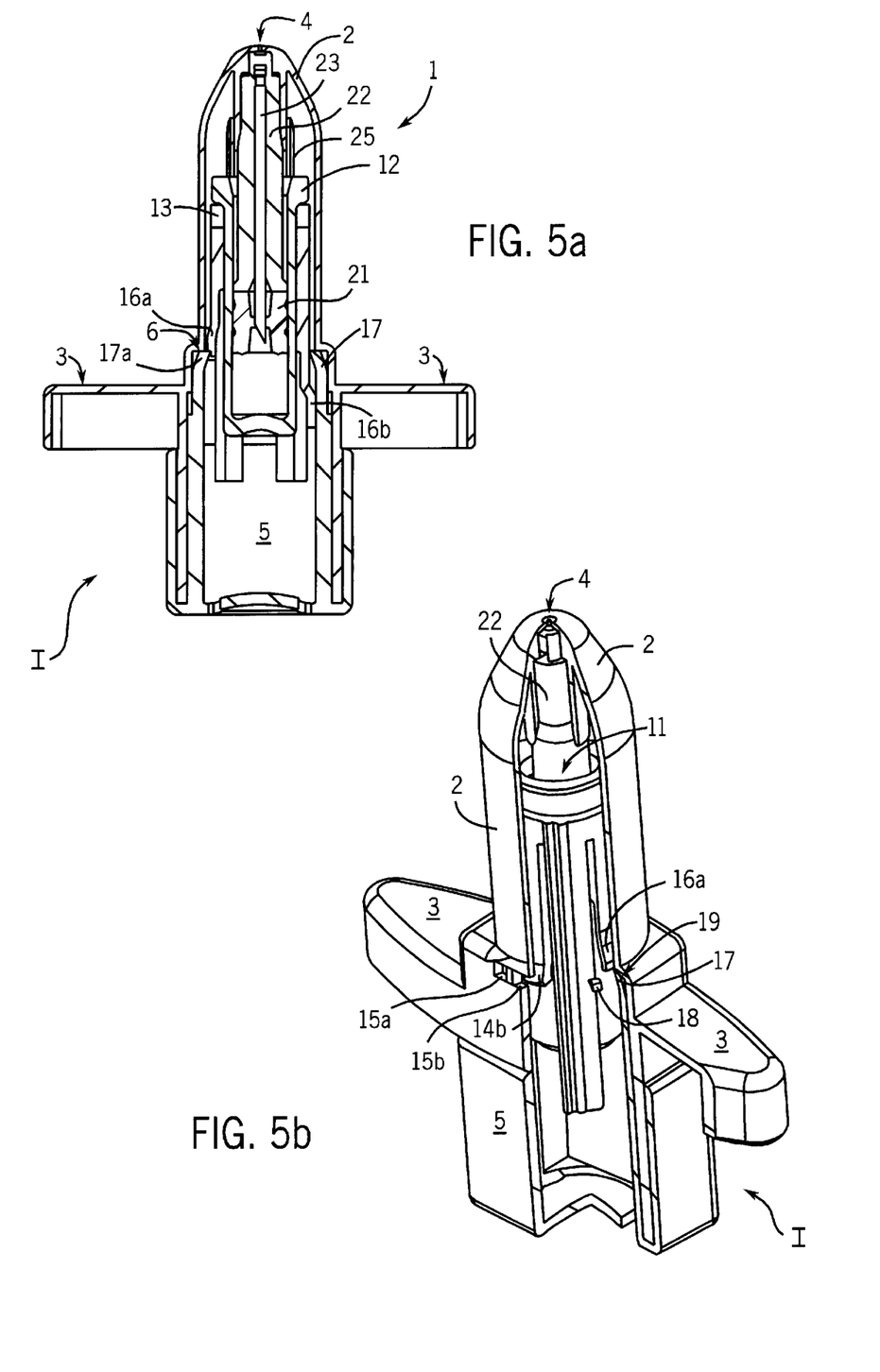
FIGS. 5a and 5b show the position of the operating presser in the operating end position after the first stroke.

FIGS. 5*a* and 5*b* show the position reached when a first stroke has taken place. The pump cylinder 11 of the thrust piston pump 10 has been moved in the direction of the discharge opening 4 by the cooperation between the spring web 16*a* and driver 17*a*. The needle 23 has perforated the piston 21 and forms a discharge channel to the discharge opening 4 of the casing 2. Following the perforation of the piston 21 by the needle 23 the shaft 22 engages on the piston 21 and over the path of a stroke presses it in the direction of the bottom of the glass ampoule 12 held in the sleeve 13. The operating presser 5 is once again in the operating end position I, the overpressable spring web 16*a* still engaging with the driver 17. To secure the pump cylinder 11 prior to a movement counter to the stroke direction and consequently also for ensuring a suction of air into the glass ampoule 12 the locking cam 14*b* locks in the locking hole 15*b* of the casing 2. There is no longer an engagement of the locking cam 14*a* in the locking hole 15*a*. On reaching the operating end position the pressure point means 18 for the second stroke engage on the casing shearing edge 19*b*. The prevention of the shearing of the pressure point means 18 for the second stroke on the shearing edge 19 and the overtravel of the operating end position I is ensured by the first stop 6 for the operating presser 5 on the casing 2. To enable a second stroke of the thrust piston pump 10 to take place, the user of the dispenser must initially manually bring the operating presser 5 into the operating starting position II.

The manual operation of the operating presser 5 for bringing the operating presser out of the operating end position I and into the operating starting position II can be replaced by a force reservoir or accumulator, particularly in spring form, said force reservoir being tensioned in the operating end position I. In order to ensure a deliberate, planned bringing of the operating presser into the operating starting position II, holding means are provided, which releasably fix the tensioned position of the forced reservoir, are lease member being provided either on the casing 2 or on the operating presser 5, during whose operation the operating presser 5 is brought into the operating starting position II. Ideally the force reservoir is pretensioned prior to the bringing of the operating presser 5 for the first time into its operating starting position II. The release member is then preferably constructed as a tamper-proof seal (i.e. only operable in an obvious and usually irreversibly damaged manner) or prior to operation such a tamper-proof seal must be removed. It is also advantageous if the holding means only act on the force reservoir prior to the first operating stroke and following each operating stroke the operating presser 5 is brought back into the operating starting position II without any further operation of the release member. In the simplest construction the holding means and release member are constructed as a tear-off web connected by means of predetermined breaking points both to the operating presser 5 and casing 2. Prior to the use of the dispenser this tear-off web must be torn off by the user, after which the operating presser 5 is brought into the operating starting position I through the action of the force reservoir.

Figures 6A, 6B:
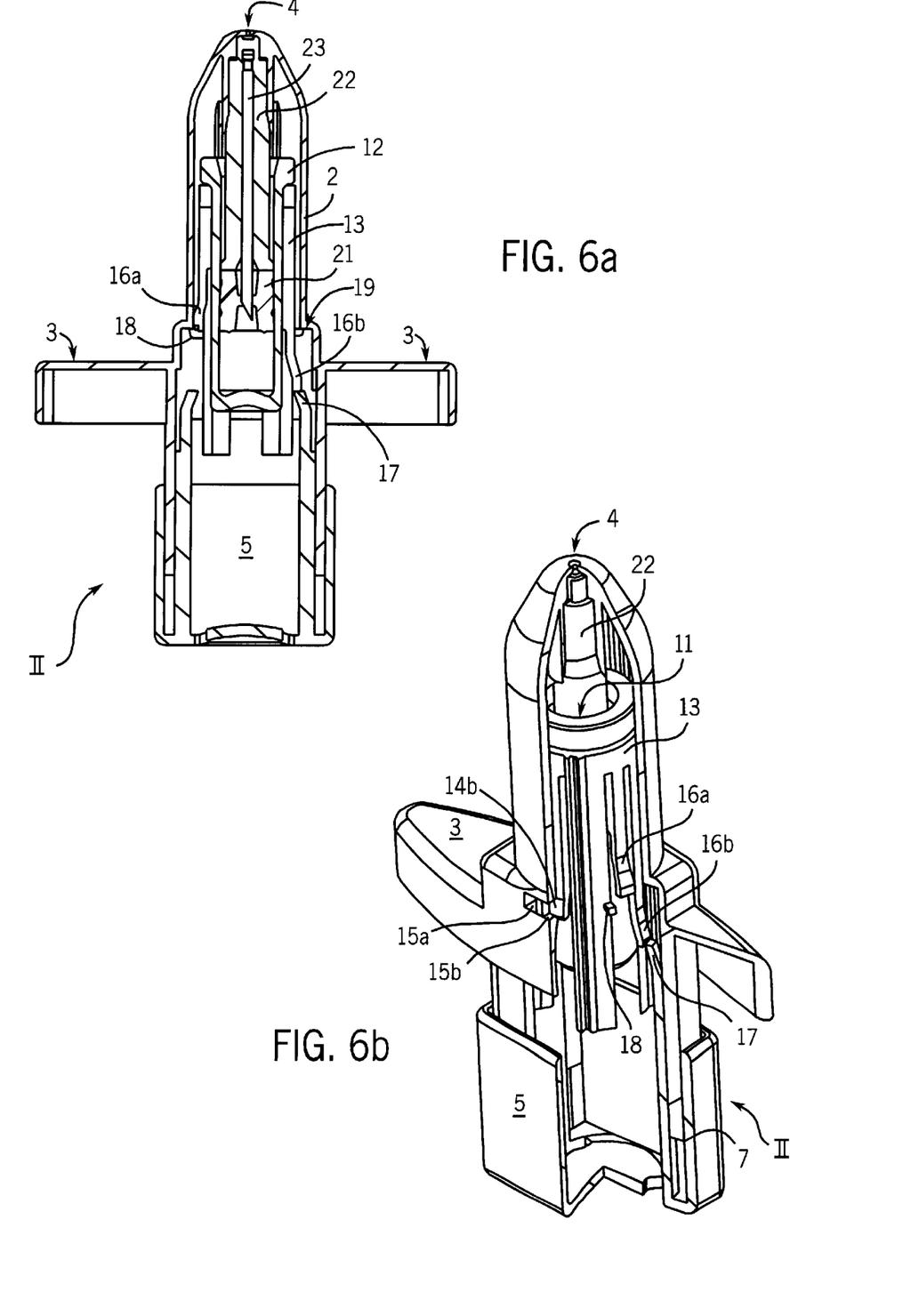
FIGS. 6a and 6b show the position of the operating presser in the operating starting position before the second stroke.

FIGS. 6*a* and 6*b* show the operating presser 5 in the operating starting position II prior to the second stroke. The sleeve 13 and the glass ampoule 12 held therein remain in an unchanged position with respect to the casing 2. The needle 23 located in the shaft 22 still traverses the piston 21 and consequently forms a discharge channel from the ampoule interior to the discharge opening 4 of the casing 2. The position of the sleeve 13 in the casing 2 is secured by the locking cam 14*b* engaging in the locking hole 15*b*, whilst the operating presser 5 is manually brought by the operator counter to the stroke direction out of the operating end position I shown in FIGS. 5*a* and 5*b* into the operating starting position II. On reaching the operating starting position II the driver 17 engages with the spring web 16*b*, which forms a drag means for the sleeve 17 with the operating presser 5. The pressure point means 18 for the second stroke are in engagement with the shearing edge 16 constructed on the casing 2 of the dispenser 1. The spring web 16*a* slides in inwardly engaging manner in the casing 2 and is no longer in engagement. According to a preferred, not shown embodiment it is also possible for the overpressable spring web 16*a*, which during the first stroke for carrying along the sleeve with the stroke movement of the operating presser 5, is used during a following stroke as a locking cam for fixing the position of the sleeve 13 with respect to the casing 2.

Figure 7A:
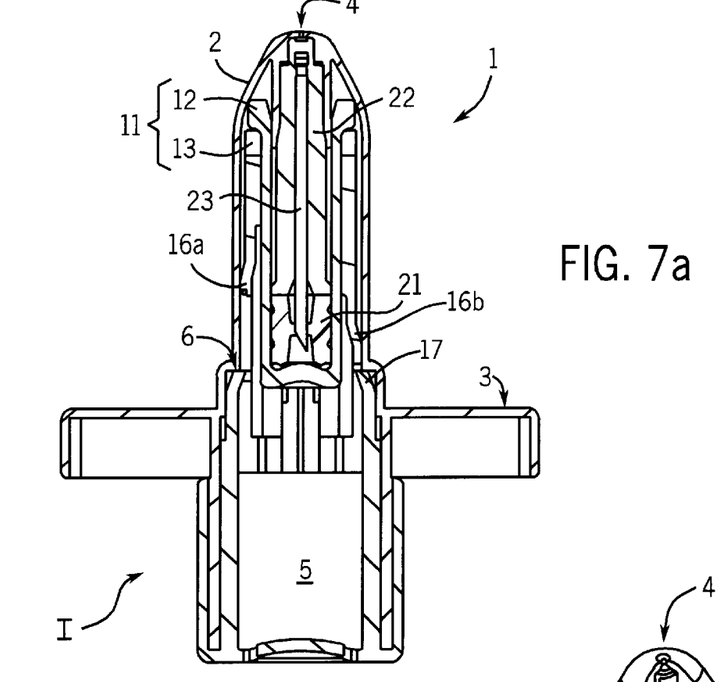
FIGS. 7a and 7b show the position of the operating presser in the operating end position after the second stroke.
Figure 7B:
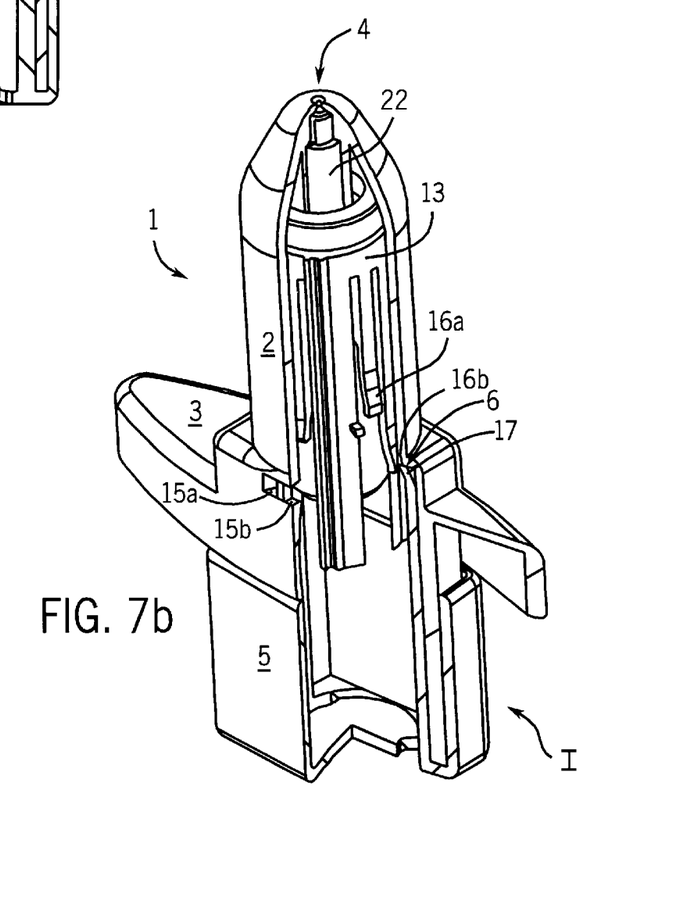

FIGS. 7*a* and 7*b* show the operating end position at the end of the second, and in the represented embodiment last, stroke of the operating presser 5 and thrust piston pump 10.

Through the second operation of the operating presser the pressure point means 18 (shown in FIGS. 6*a* and 6*b*) are sheared at the shearing edge 19. This ensures that also during the second stroke the operating presser is moved up to the first stop 6, so that the operating end position I is reached. The piston 21 perforated by the needle 23 during the stroke movement of the pump cylinder 11, comprising the glass ampoule 12 and sleeve 13, is immersed to such an extent in the ampoule 12 that its base is reached. The second partial charge of the medium to be discharged located in the glass ampoule is discharged from the dispenser by means of the needle 23 and discharge opening 4. The pump cylinder 11 is carried along by means of the driver 17 constructed on the operating presser 5 and in operative connection with the overpressable spring web 16*b*. During the operation of the operating presser 5 the locking connection between the sleeve 13 and the casing 2 of dispenser 1 is released. A further securing of the represented operating end position of the sleeve 13 in casing 2 is no longer necessary when the final discharge stroke has been performed. Thus, in this position there are no locking cams shaped on the sleeve in engagement with the locking holes formed in the casing 2 of dispenser 1. However, the driver 17 is still in contact with the spring web 16*b* in the operating end position, but without being in the position to perform a further stroke movement. This is impossible because the mounting of the piston 21 on the bottom of the glass ampoule 12 also prevents an axial movement in the direction of the casing discharge opening, in the same way as the engagement of the driver 17 on the first stop 6.

The dispenser 1 is generally operated by the thumb on the operating presser 5 and index and middle finger on the gripping surface 3. Dispensers which, in a single stroke or in a small number of partial strokes, discharge a charge and which hermetically seal the charge up to the first operation of the dispenser, frequently contain medicaments or vaccines, which are kept by the patient for immediate use. Thus, e.g. medicaments are applied to the nasal mucosa, because from there they pass in the fastest and most compatible manner into the blood stream. In particular, medicaments for combatting migraine and other headaches are administered in this way. The discharge device according to the invention makes it possible to discharge the individual partial charges with a high dosing precision and reliability and, if desired, also in measured, differing quantities. The partial strokes differ due to the idle path to be traversed during the initial operation, which must be borne in mind during design, particularly when dimensioning the overpressable spring webs and the position of the driver. Besides medicaments to be applied to the nose (to the nasal mucosa), the dispenser is also suitable for medicaments intended for the eyes or other application locations occurring in pairs or in multiple form. The dispenser can also be used for several successive applications in the form of a spray or other delivery form, e.g. the treatment at intervals of a few minutes at the same application point.

What is claimed is:

1. Dispenser comprising a discharge device for the discharge of an optionally atomized medium in a plurality of discharge strokes, said dispenser further comprising an operating presser for operating the discharge device, wherein prior to each of said plurality of discharge strokes, the operating presser is positioned at an operating end position for a respective discharge stroke, said operating presser being responsive to a return force to be moved into an operating starting position prior to commencing a next discharge stroke, said starting position being common to each respective discharge stroke.

2. Dispenser according to claim 1, wherein the dispenser has a casing with a gripping surface shaped thereon for supporting at least one finger of a user and with a discharge opening, the operating presser being guided in relatively movable manner to the gripping surface on the casing.

3. Dispenser according to claim 2, wherein the relative movement is a linear movement.

4. Dispenser according to claim 1, wherein the operating end position is fixed by a first stop for limiting the stroke movement of the operating presser.

5. Dispenser according to claim 1, wherein the operating starting position is fixed by a second stop for limiting the movement in a direction opposite a direction of the discharge stroke.

6. Dispenser according to claim 1, wherein the discharge device comprises a thrust piston pump, whose pump cylinder is the reservoir for a medium to be discharged.

7. Dispenser according to claim 6, wherein the pump cylinder comprises a cylindrical glass ampoule inserted in a sleeve.

8. Dispenser according to claim 6, wherein cooperating locking means are formed on the pump cylinder and the casing to prevent a movement of the pump cylinder in opposition to the discharge stroke movement.

9. Dispenser according to claim 8, wherein the locking means interengage when the operating presser reaches the operating end position.

10. Dispenser according to claim 8, in which locking means act between the pump cylinder and casing and are constructed for preventing a pump cylinder movement counter to the discharge stroke movement and in which drag means acting between the operating presser and pump cylinder are constructed for carrying along the pump cylinder during the stroke movement of the operating cylinder, wherein the pump cylinder-side parts of the drag means are constructed to operate as pump cylinder-side locking means during a subsequent operation of the dispenser.

11. Dispenser according to claim 6, wherein cooperating drag means are formed on the pump cylinder and operating presser, so that the pump cylinder is carried along during a stroke of the operating presser (5).

12. Dispenser according to claim 11, wherein the drag means come into operative connection when said operating presser is in the operating starting position.

13. Dispenser according to claim 11, wherein the drag means are constructed in such a way that the drag connection is released during a movement in opposition to the discharge stroke movement.

14. Dispenser according to claim 1, wherein the movement of the operating presser from the operating end position into the operating starting position results from a manually provided return force.

15. Dispenser according to claim 1, wherein the movement of the operating presser from the operating end position into the operating starting position results from pressure provided from a force reservoir.

16. Dispenser according to claim 15, wherein the force reservoir is kept pretensioned in the operating end position by holding means, which are releasable by the operation of a release member, so that a movement of the operating presser from the operating end position to the operating starting position takes place.

17. Dispenser according to claim 16, wherein during, or prior to, the first operation of the release member, a tamper-proof seal is irreversibly destroyed.

18. Dispenser according to claim 16, wherein the holding means only keep the force reservoir pretensioned prior to the first operation of the release member.

19. Dispenser according to claim 18, wherein the release member and the holding means are constructed as a tear-off web connected on either side by means of predetermined breaking points to the casing and operating presser.

20. Dispenser according to claim 1, wherein the operating presser has a rectangular cross-section.

21. Dispenser according to claim 20, wherein the casing has a rectangular cross-section in the area of the operating presser.

22. Dispenser according to claim 1, wherein pressure point means are provided containing predetermined breaking material bridges acting between the casing and the pump cylinder.

23. Dispenser according to claim 1, wherein the discharge device constructed as a thrust piston pump has a piston, which is formed by a perforatable plug forming a closure for the pump cylinder of the thrust piston pump and which is preferably irreversibly pressable into the pump cylinder by a shaft mounted in the discharge section and is perforatable by a needle held in the shaft.

* * * * *